(12) United States Patent
De Gier

(10) Patent No.: US 10,035,148 B2
(45) Date of Patent: *Jul. 31, 2018

(54) DEVICE FOR USE IN MOLECULAR DIAGNOSTICS TESTING

(71) Applicant: KONINKLIJKE PHILIPS N.V., Eindhoven (NL)

(72) Inventor: Ronald Cornelis De Gier, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/669,224

(22) Filed: Mar. 26, 2015

(65) Prior Publication Data

US 2015/0196916 A1    Jul. 16, 2015

Related U.S. Application Data

(63) Continuation of application No. 13/003,010, filed as application No. PCT/IB2009/053031 on Jul. 13, 2009, now Pat. No. 8,992,856.

(30) Foreign Application Priority Data

Jul. 14, 2008  (EP) ..................... 08160333
Nov. 24, 2008  (EP) ..................... 08169800

(51) Int. Cl.
*B01L 3/00*     (2006.01)
*G01N 35/10*    (2006.01)

(52) U.S. Cl.
CPC ............ *B01L 3/523* (2013.01); *G01N 35/109* (2013.01); *G01N 35/1002* (2013.01); *G01N 35/1079* (2013.01)

(58) Field of Classification Search
CPC .................. B01L 3/523; G01N 35/1002; G01N 35/1079; G01N 35/109
See application file for complete search history.

(56) References Cited

U.S. PATENT DOCUMENTS

| 4,304,257 A | 12/1981 | Webster |
| 4,848,722 A | 7/1989 | Webster |
| 4,889,613 A | 12/1989 | McNeal et al. |

(Continued)

FOREIGN PATENT DOCUMENTS

| EP | 0706003 A2 | 4/1996 |
| GB | 2400158 A | 10/2004 |

(Continued)

*Primary Examiner* — Brian R Gordon

(57) ABSTRACT

A device for use in molecular diagnostics testing includes at least one sealed reagent storage container, and at least one opener for unsealing the reagent storage container. The device further includes an actuator coupled to the reagent storage container and opener such that moving the actuator brings the reagent storage container and the opener together so that the opener unseals the reagent storage container. In addition, a locking unit is configured to prevent movement of the reagent storage container and the opener towards each other in a locked position and to allow the movement in an unlocked position, where moving the actuator moves the actuator between the locked position and the unlocked position.

10 Claims, 7 Drawing Sheets

(56) References Cited

U.S. PATENT DOCUMENTS

| | | | |
|---|---|---|---|
| 4,974,457 A * | 12/1990 | Angst | G01N 35/1079 73/863.81 |
| 5,077,013 A | 12/1991 | Guigan | |
| 5,935,523 A * | 8/1999 | McCandless | G01N 35/1079 141/330 |
| 6,135,172 A | 10/2000 | Fere et al. | |
| 6,360,794 B1 * | 3/2002 | Turner | G01N 35/1079 141/1 |
| 6,527,003 B1 | 3/2003 | Webster | |
| 6,627,156 B1 * | 9/2003 | Goodale | G01N 35/1079 220/277 |
| 7,445,753 B1 | 11/2008 | Kreis et al. | |
| 7,858,041 B2 * | 12/2010 | Muraishi | B01L 3/021 422/511 |
| 8,758,702 B2 * | 6/2014 | Blouin | B01L 3/021 422/106 |
| 8,992,856 B2 * | 3/2015 | De Gier | G01N 35/109 422/430 |
| 2002/0037221 A1 | 3/2002 | Mastrangelo et al. | |
| 2003/0030023 A1 | 2/2003 | Wang et al. | |
| 2004/0217059 A1 | 11/2004 | Coville et al. | |
| 2011/0127294 A1 | 6/2011 | Pearcy et al. | |
| 2015/0196916 A1 | 7/2015 | De Gier | |

FOREIGN PATENT DOCUMENTS

| | | |
|---|---|---|
| JP | H0618383 A | 10/1985 |
| JP | 8015279 A | 1/1996 |
| JP | 11183484 A | 7/1999 |
| JP | 2006125978 A | 5/2006 |
| WO | 2007093939 A1 | 8/2007 |

* cited by examiner

DEVICE FOR USE IN MOLECULAR DIAGNOSTICS TESTING

CROSS REFERENCE TO RELATED APPLICATION

This is a divisional of prior application Ser. No. 13/003,010 filed Jan. 7, 2011.

FIELD OF THE INVENTION

The invention relates to a device for use in molecular diagnostics testing.

BACKGROUND OF THE INVENTION

In systems for molecular diagnostics reagents can be stored in a container, for instance inside a disposable system. To guarantee a reasonable shelflife the container needs to have sufficient barrier properties. This leads most often to hermetically closed containers that fulfill the lifetime requirements but make it hard to access the stored reagents. An example of a molecular diagnostics system comprising a reagent storage container is found in WO093939.

SUMMARY OF THE INVENTION

It is an object of the invention to provide a device for use in molecular diagnostics testing in which a reagent can be stored in a reagent storage container under sealed conditions prior to use and in which the reagent storage container can be unsealed when the reagent is needed for testing. The device according to the invention comprises at least one reagent storage container that is sealed prior to use. The device further comprises at least one opener for unsealing the reagent storage container when the stored reagent is needed for testing. When the reagent is needed, an actuator is operated by a person using the device. The actuator is coupled to at least one of the reagent storage container and the opener. As a result of operating the actuator, the reagent storage container and the opener are moved together. As a consequence hereof, the opener can unseal the reagent storage container, for instance by piercing a foil sealing the reagent storage container with a pointed tip.

An embodiment of the device according to the invention is characterized in that the actuator is part of a manifold selectively coupleable to a reagent storage container for removing content from the reagent container.

This embodiment has the advantage that sometimes devices for use in molecular diagnostics testing already comprise a manifold to selectively couple to a reagent storage container. The operation of the manifold, for instance, to selectively couple to a reagent storage container may be used to open one or more reagent container(s) in one go, making operation of such devices simpler. Once a connection to the selected reagent storage container has been established, at least part of the contents of the reagent storage container is taken out (for instance by using a plunger comprised in the manifold). Next, the manifold is operated to couple to a process chamber and contents taken from the reagent storage container is passed from the manifold into the process chamber (for instance by again using the aforementioned plunger). At that time, the process chamber comprises a sample to be processed, the processing requiring the presence of the added reagent. Selecting a reagent storage container often involves rotating the manifold, or some other motion of the manifold. This embodiment has the advantage that it uses motion of the manifold, a feature that is already present in some devices, for unsealing a reagent storage container.

A further embodiment of the device according to the invention is characterized in that the actuator is rotatable.

This embodiment has the advantage that compact construction of the device is possible as the actuator can stay in a single location during its operation.

A further embodiment of the device according to the invention is characterized in that the actuator is coupled to at least one of the reagent storage container and the opener using a cable that is pulled by moving the actuator.

This embodiment has the advantage that a cable provides an easy and flexible means for coupling the actuator to at least one of the reagent storage container and the opener. The flexibility offered by a cable enables that the actuator can be coupled to at least one of the reagent storage container and the opener around bends and other obstacles.

A further embodiment of the device according to the invention is characterized in that the actuator is coupled to at least two reagent storage containers and/or at least two openers using cables of different lengths.

This embodiment has the advantage that it allows different reagent storage containers to be unsealed at different times.

A further embodiment of the device according to the invention is characterized in that the actuator is coupled to at least one of the reagent storage container and the opener using an actuation plate, the actuation plate comprising a trajectory along which one of the reagent storage container and the opener is moved towards the other of the reagent storage container and the opener.

This embodiment has the advantage that it provides an easy means for moving a reagent storage container and an opener towards each other, especially if multiple reagent storage containers need to be unsealed. Multiple reagent storage containers and/or multiple openers can be moved using a single actuation plate.

A further embodiment of the device according to the invention is characterized in that the actuation plate comprises different trajectories for different reagent storage containers and/or different openers.

This embodiment has the advantage that different trajectories allow different reagent storage containers and/or different openers to be moved towards each other at different speeds, allowing different reagent storage containers to be opened at different times.

A further embodiment of the device according to the invention is characterized in that the actuation plate further comprises a further trajectory intersecting a trajectory along which one of the reagent storage container and the opener is moved towards the other of the reagent storage container and the opener at a point at which the reagent storage container and the opener reach their final positions relative to each other.

This embodiment has the advantage that it allows using the actuator as part of a manifold.

A further embodiment of the device according to the invention is characterized in that the actuator is coupled to at least one of the reagent storage container and the opener using a rotationally asymmetrical actuation ring, the actuation ring forcing at least one of the reagent storage container and the opener towards the other of the reagent storage container and the opener.

This embodiment has the advantage that it provides an easy means for moving a reagent storage container and an opener towards each other.

A further embodiment of the device according to the invention is characterized in that the actuation ring comprises a protrusion for moving one of the reagent storage container and the opener towards the other of the reagent storage container and the opener.

This embodiment has the advantage that easy means for moving a reagent storage container and an opener towards each other.

A further embodiment of the device according to the invention is characterized in that the device comprises at least two actuation rings coupled to different reagent storage containers and/or different openers.

This embodiment has the advantage that it allows the amount of motion of the actuator needed to unseal a reagent storage container to be individualized for individual reagent storage containers.

A further embodiment of the device according to the invention is characterized in that the actuator comprises a thread for moving the reagent storage container and the opener towards each other.

This embodiment has the advantage that it provides an easy way for moving the reagent storage container and the opener towards each other, especially if the actuator is a rotatable manifold.

A further embodiment of the device according to the invention is characterized in that the actuator comprises a shaped ring, the shaped ring comprising a non-flat shaped surface facing at least one of the reagent storage container and the opener for moving the reagent storage container and the opener towards each other in the direction of the axis of rotation of the actuator.

This embodiment has the advantage that it provides an alternative to a thread and, additionally, allows sequential opening of different reagent storage containers depending on the exact shape of the non-flat shaped surface. The steeper, for instance, undulations on the non-flat shaped surface, the quicker a reagent storage container and an opener are moved towards each other.

A further embodiment of the device according to the invention is characterized in that the device comprises locking means for temporarily preventing the reagent storage container and the opener from moving towards each other.

This embodiment has the advantage that it reduces the risk of unintended opening of a reagent storage container. Obviously, it is not intended to open a reagent storage container during storage of the reagent storage container. Locking means can prevent unintended opening and after unlocking or removal of the locking means, a reagent storage container can be opened for use.

A further embodiment of the device according to the invention is characterized in that the device is a cartridge insertable into a device for molecular diagnostics testing. This embodiment has the advantage that a cartridge insertable into a device for molecular diagnostics testing is more flexible than a device for molecular diagnostics testing into which a sample to be tested is inserted directly, that is without being inserted into a cartridge first. Moreover, a cartridge for a use in molecular diagnostics testing would benefit from any one of the previous embodiments.

DETAILED DESCRIPTION OF EMBODIMENTS

Figure 1:
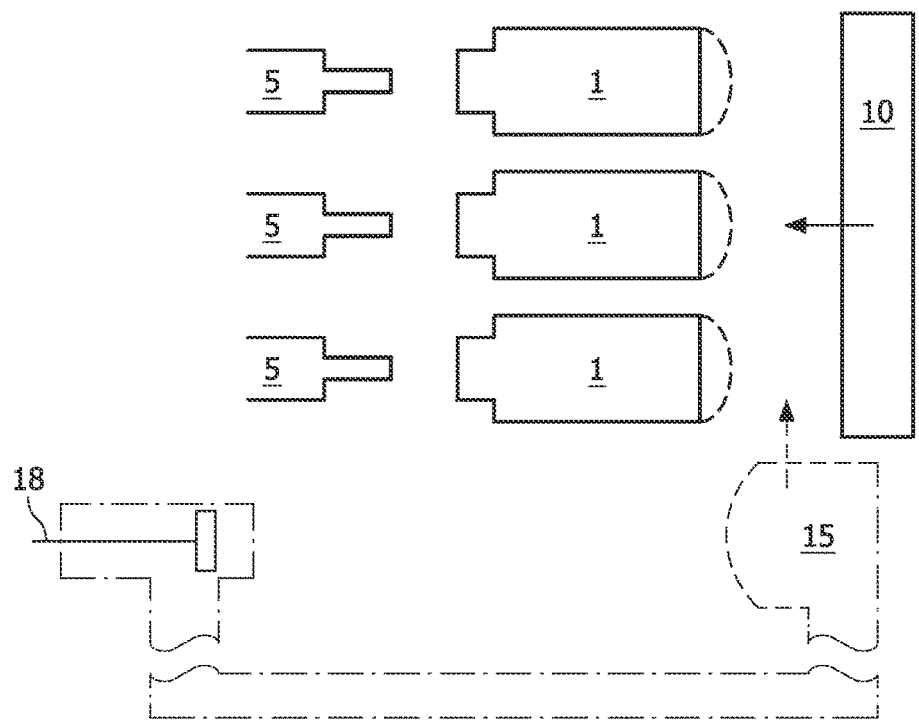
FIG. 1 schematically shows a device according to the invention comprising an actuator that can be translated.

FIG. 1 schematically shows a device according to the invention comprising an actuator that can be translated. The present figure shows reagent storage containers 1, openers 5, and an actuator 10. The reagent storage containers 1 and the openers 5 are movable towards each other, for instance, by mounting the reagent storage containers 1 and/or the openers 5 on a rail like construction (not shown). The actuator 10 is movable in a direction towards the openers 5 and 10, for instance, the manually operated by a person using the device in FIG. 1. Moving the actuator 10 towards the openers 5, the actuator 10 pushes the reagent storage containers 1 towards the openers 5. As in all embodiments shown in this document, the openers 5 comprise means for unsealing the reagent storage containers 1 such as, for instance, a pointed tip, a hollow needle, etc. In the present embodiment, the tip pierces a seal on the reagent storage containers 1, after which reagents stored in the reagent storage containers 1 can be removed from the reagent storage containers 1. If the pointed tips comprise, for instance, hollow needles, removing reagents from the reagent storage containers 1 can be achieved by transporting the reagents through the hollow needles and then onwards towards the locations where the reagents are needed.

An alternative arrangement is shown using the dashed lines. Actuator 15 is movable along the reagent storage containers 1 which, in this particular embodiment, have protrusions for core operating with the actuator 15. As the actuator 15 moves along the reagent storage containers 1 it pushes the reagent storage containers 1 towards the openers 5. The protrusions allow the actuator 15 to push a specific reagent storage container 1 towards a corresponding opener 5 while, at the same time, allowing the actuator 15 to continue on to the next reagent storage container 1. The distance between a specific reagent storage container 1 and its corresponding opener 5 on the one hand and the dimensions of the actuator 15 and the protrusion only specific reagent storage container 1 on the other hand need to be chosen such that after the actuator 15 has passed a protrusion, the reagent storage container 1 is moved close enough to its corresponding opener 5 that the reagent storage container 1 can be unsealed and its contents removed. In the present figure, the distance between the reagent storage containers and the corresponding openers 5 has been chosen too large for clarity.

Use of the actuator 15 has the advantage that the relative position of a reagent storage container 1 and its corresponding opener 5 remain unchanged after the actuator 15 has passed a specific reagent storage container 1. Once moved towards each other, the relative position of a reagent storage container 1 and its corresponding opener 5 remains unchanged. This has the advantage that the actuator 15 may be arranged to form a manifold that can couple selectively to one of the reagent storage containers 1. The manifold variant is indicated by the dashed/dotted addition to the actuator 15. Once moved along all the reagent storage containers 1, the actuator 15 (now acting as a manifold) can coupled to a specific opener 5 after which reagent can be removed from the reagent storage container 1 coupled to that specific opener 5. The reagent may be removed from the reagent storage container 1 using a plunger 18 integrated into the actuator 15. After reagent has been removed from a reagent storage container 1 the actuator 15 may be coupled to a process chamber (not shown) into which the removed reagent is inserted. Once in the process chamber, the reagent can be used for molecular diagnostics testing.

It will be clear to a person skilled in the art that the protrusions need not necessarily be located on the side of the reagent storage containers 1 that faces away from the openers 5. The protrusions may, for instance, also be positioned as the protrusions 55 in FIGS. 3-5. Moreover, one might even do without protrusions at all. What matters is that the reagent storage containers 1 comprised a location on which an actuator can exert force and which allowed, if need be, an actuator to move from one reagent storage container 1 to the next (as is the case with the actuator 15, but not with the actuator 10). Furthermore, it will be clear to a person skilled in the art that further variations on the arrangement shown in FIG. 1 are possible as well. For instance, the actuator 10 (or, alternatively, the actuator 15) may be arranged to act on the openers 5 instead of on the reagent storage containers 1 for moving the reagent storage containers 1 and the openers 5 towards each other.

Figure 2:
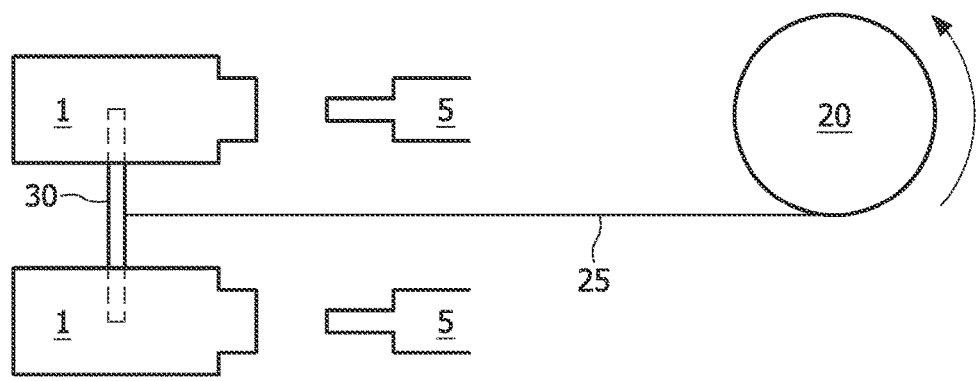
FIG. 2 schematically shows a further device according to the invention comprising a rotatable actuator coupled using a cable.

FIG. 2 schematically shows a further device according to the invention comprising a rotatable actuator coupled using a cable. The present figure again shows reagent storage containers 1 and openers 5, just as in FIG. 1. However, in the present figure there is a rotatable actuator 20. Similar to the actuator 10 and the actuator 15 shown in FIG. 1, the actuator 20 may be manually operated by a person operating the device shown in FIG. 2. The actuator 20 is coupled to the reagent storage containers 1 using cable 25 and bar 30. As the actuator 20 is rotated counter clockwise, the reagent storage containers 1 are pulled towards the openers 5. Again, just as in FIG. 1, the openers 5 comprise means for unsealing the reagent storage containers 1.

Figure 4:
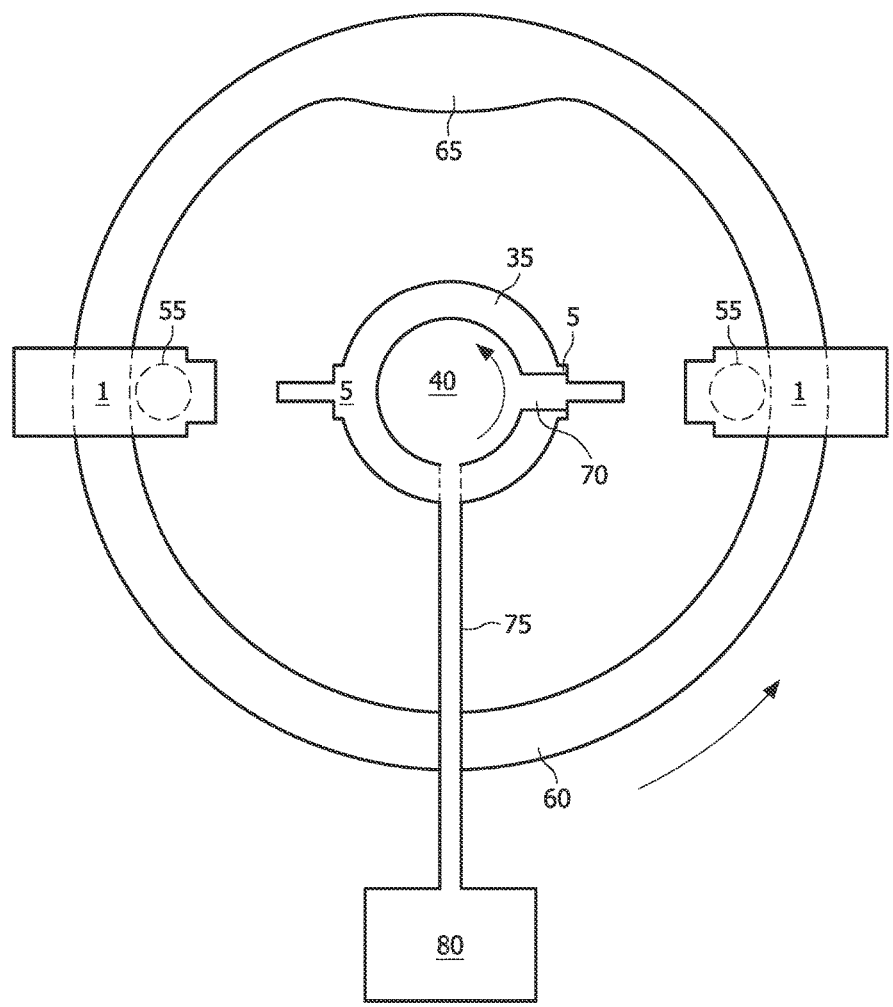
FIG. 4 schematically shows a further device according to the invention comprising a rotationally asymmetrical actuation ring.
Figure 5:
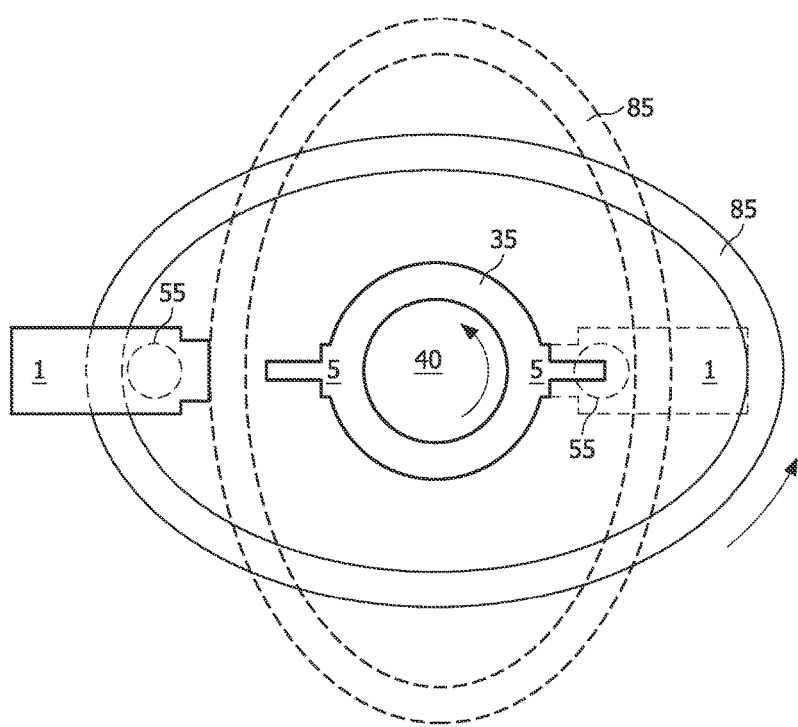
FIG. 5 schematically shows a further device according to the invention comprising a different rotationally asymmetrical actuation ring.

If the cable 25 is provided with enough slack, the actuator 20 may rotate further (both clockwise and counter clockwise) within the limits of the amount of slack provided after a reagent storage container 1 has been unsealed by its corresponding opener 5 without affecting the relative position of the reagent storage container 1 and its corresponding opener 5. Once moved towards each other, the relative position of a reagent storage container 1 and its corresponding opener 5 remains unchanged. This has the advantage that the actuator 20 may be arranged to form a manifold that can couple selectively to one of the reagent storage containers 1. A rotatable actuator arranged to act as manifold is shown in FIGS. 4 and 5. The difference between these two figures and the present figure is that in the present figure the actuator 20 is coupled to the reagent storage containers 1 using a cable 25 instead of the actuation ring 60 in FIG. 4 and the actuator ring 85 in FIG. 5.

It will be clear to a person skilled in the art that variations to the arrangement shown in FIG. 2 are possible. For instance, the reagent storage containers 1 and the openers 5 may exchange positions so that the actuator 20 exerts a force on the openers 5 instead of on the reagent storage containers 1. Another variation is that the reagent storage containers 1, or in the previous variation the openers 5, are coupled individually to the actuator 20 using individual cables. In the latter of variation, cables of different lengths may be used for different couplings. In this way, different reagent storage containers 1 may be unsealed at different times by requiring the actuator 20 to be rotated over different angles.

Figure 3:
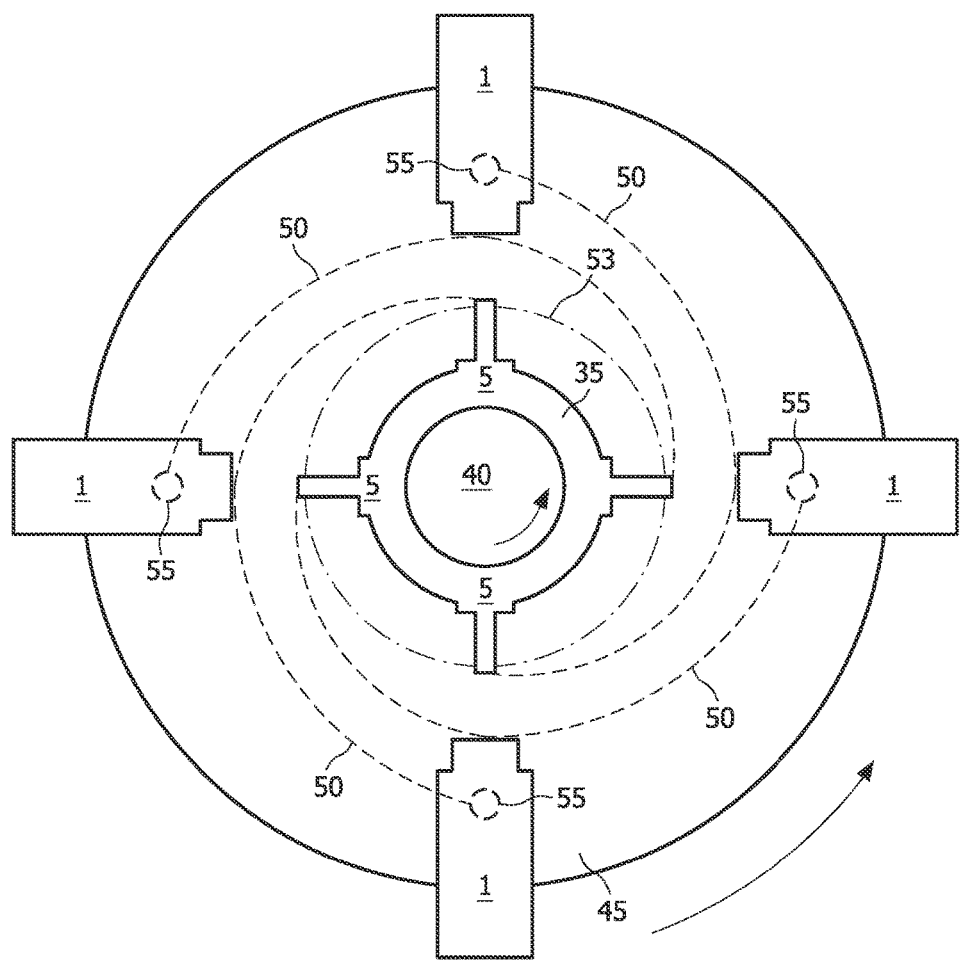
FIG. 3 schematically shows a further device according to the invention comprising an actuation plate.

FIG. 3 schematically shows a further device according to the invention comprising an actuation plate. The present figure again shows reagent storage containers 1 and openers 5, just as in FIG. 1. In the present figure in the reagent storage containers 1 comprise protrusions 55. In this particular embodiment, the protrusions 55 have been arranged on the sides of the reagent storage containers 1 facing away from the viewer. Consequently, the protrusions 55 have been indicated by dashed circles. In the present figure, the openers 5 are comprised in housing 35. The housing 35 houses a rotatable actuator 40. The actuator 40 is coupled to the actuation plate 45. As the actuator 40 is rotated, the actuation plate 45 rotates with it. The actuation plate 45 comprises trajectories for guiding the reagent storage containers 1 towards the openers 5. The trajectories have been schematically indicated by the dashed curves 50, 53. The trajectories spiral towards the centre of the actuation plate 45. The trajectories may comprise, for instance, a groove or a ridge. The reagent storage containers 1 are movable along straight lines running through the centre of the actuator 40. If the trajectories comprise grooves, the protrusions 55 enter their respective grooves and follow the trajectories. Consequently, the reagent storage containers 1 are moved towards the openers 5 as the actuator 40 and, consequently, the actuation plate 45 rotate counter clockwise. If the trajectories comprise ridges, the ridges contact the protrusions 55 on the sides of the protrusions 55 that face away from the centre of the actuator 40. As the actuator 40 and, consequently, the actuation plate 45 rotate counter clockwise, the protrusions 55 slide along the ridges moving the reagent storage containers 1 towards the openers 5.

The actuation plate 45 can be adapted to allow further rotation (both clockwise and counter clockwise) of the actuator 40 after the reagent storage containers 1 have been unsealed by their respective openers 5. To this end, the actuator plate 45 comprises the dashed/dotted trajectory. This latter trajectory intersects the points of the other trajectories at which the reagent storage containers 1 reach their final positions relative to their respective openers 5. If the spiraling trajectories comprise grooves, the dashed/dotted trajectory comprises a circular groove. Once the reagent storage containers 1 reach their final positions relative to their respective openers 5, the protrusions 55 enter the dashed/dotted trajectory. The actuator 40 and, consequently, the actuation plate 45 can then rotate without affecting the positions of the reagent storage containers 1 relative to their respective openers 5. If the spiraling trajectories comprise ridges, the dashed/dotted trajectories comprise an opening in or termination of the ridges. Once the reagent storage containers 1 reach their final positions relative to their respective openers 5, the protrusions 55 enter the dashed/dotted trajectory. Rotation of the actuator 40 and, consequently, of the actuation plate 45 then no longer affects the positions of the reagent storage containers 1 relative to their respective openers 5. The dashed/dotted trajectory allows the housing 35 and the actuator 40 to be adapted to function as a manifold. The manifold can selectively couple to one of the reagent storage containers 1 to remove reagent from that reagent storage container 1. Removal may take place using, for instance, a plunger integrated into the manifold. After removal of the reagent, the manifold can be coupled to a process chamber in which the reagent is used during testing. Adapting the housing 35 in the actuator 40 to function as a manifold is further discussed in relation to FIG. 4.

It will be clear to a person skilled in the art that variations on the arrangement shown in FIG. 3 are possible. For instance, the positions of the reagent storage containers 1 and the openers 5 may be reversed. In another variation, the openers 5 may be arranged to move outwards from the centre of the actuator 40 along trajectories that spiral outwards instead of inwards. In a combination of the previous two variations, reagent storage containers 1 may be arranged to move outwards along outwardly spiraling trajectories towards the openers 5. With a reagent storage container 1 or an opener 5 moving outwards from the centre of the actuator 40 along a trajectory comprising a ridge, the ridge contacts the protrusion 55 on the side of the protrusion 55 facing the centre of the actuator 40. In another variation, the curvature of the trajectories is chosen to define the angle through which the actuator 40 must rotate to bring a reagent storage container 1 and its corresponding opener 5 together. The amount of curvature may be different for different trajectories.

FIG. 4 schematically shows a further device according to the invention comprising a rotationally asymmetrical actuation ring. The present figure again shows reagent storage containers 1, openers 5, housing 35, rotatable actuator 40, and protrusions 55 just as in FIG. 3. The reagent storage containers 1 are movable along straight lines through the centre of the actuator 40. However, in the present figure in the actuator 40 is coupled to actuation ring 60. As the actuator 40 rotates, the actuation ring 60 rotates with it. The actuation ring 60 comprises an actuation protrusion 65. As the actuation protrusion 65 passes a protrusion 55 during rotation of the actuation ring 60, the reagent storage container 1 coupled to that protrusion 55 is moved towards its corresponding opener 5. The distance between a protrusion 55 of a specific reagent storage container 1 and its corresponding opener 5 on the one hand and the dimensions of the actuation protrusion 65 need to be chosen such that after the actuation protrusion 65 has passed the protrusion 55, the reagent storage container 1 is moved close enough to its corresponding opener 5 that the reagent storage container 1 can be unsealed and its contents removed. In the present figure, the distance between the protrusions 55 and the corresponding openers 5 has been chosen too large for clarity.

The actuation ring 60 and its co-operation with the protrusions 55 have the advantage that the relative position of a reagent storage container 1 and its corresponding opener 5 remain unchanged if the actuator 40 and, consequently, the actuation ring 60 rotate further, after the actuation protrusion 65 has passed a specific protrusion 55. Once moved towards the centre of the actuator 40, a reagent storage container 1 remains in that position. This has the advantage that the housing 35 and the actuator 40 may be arranged to form a manifold that can couple selectively to one of the reagent storage containers 1. After rotating the actuator 40 and, consequently, the actuation ring 60 through an angle large enough to unseal a reagent storage container 1, the actuator 40 can rotate to couple the channel 70 to the unsealed reagent storage container. Next, at least part of the contents of the unsealed reagent storage container can be removed from that reagent storage container using, for instance, a plunger integrated into the manifold. The plunger may be positioned, for instance, perpendicularly to the plane of the drawing and be integrated into the actuator 40. After reagent has been removed from the unsealed reagent storage container, the actuator 40 rotates once more to couple the channel 70 to the further channel 75 (now indicated by the dashed channel) coupled to a process chamber 80. Once the channel 70 has been coupled to the further channel 75, the plunger integrated into the actuator 40 may again be used to inject reagent removed from the unsealed reagent storage container into the further channel 75 and from there into the process chamber 80. Inside the process chamber 80, the reagent may be used, for instance, in molecular diagnostics testing.

It will be clear to a person skilled in the art that variations to the arrangement shown in the present figure are possible. In one variation, the actuation ring 60 comprises at least two actuation protrusions 65. With more than one actuation protrusion 65 the angle through which the actuator 40 must rotate before a reagent storage container 1 is unsealed become smaller than with only one actuation protrusion 65. In a further variation the number of reagent storage containers 1 and openers 5 different from the two reagent storage containers 1 and openers 5 shown in FIG. 4. In yet a further variation, an actuation ring having an actuation protrusion that faces away from the centre of the actuator 40 instead of towards the centre of the actuator 40 as in the present figure may be used to move the openers 5 outwards towards the reagent storage containers 1. In these variations care needs to be taken to ensure that channel couplings are such that reagent can be removed from an unsealed reagent storage container. Usually, this will mean that a channel for removing reagent from a reagent storage container must be able to be coupled to an opener. Consequently, a further embodiment comprises an actuator coupled to an actuation ring comprising an outward facing actuation protrusion and at least one reagent storage container arranged around the actuation ring. The reagent storage containers face corresponding openers arranged along a larger circle concentric with the circle of the actuation ring. Each opener is coupled to a channel which in turn is coupled to a manifold. As the actuation ring rotates, the reagent storage containers are moved towards their corresponding openers. Once unsealed, reagent can be removed from the reagent storage containers using, for instance, a plunger integrated into the manifold. The manifold can selectively couple to one of the openers and to a process chamber into which reagent removed from a reagent storage container can be inserted. In this embodiment, the manifold and the actuator are not integrated.

FIG. 5 schematically shows a further device according to the invention comprising a different rotationally asymmetrical actuation ring. The present figure again shows reagent storage containers 1, openers 5, a housing 35, an actuator 40, and protrusions 55, just as in FIG. 4. Again, the reagent storage containers 1 are movable along straight lines through the centre of the actuator 40. Just as in FIG. 4, the arrangement of the present figure may comprise a channel 70, a further channel 75, and a process chamber 80. However, for reasons of simplicity, these elements are not shown in the present figure. The present figure shows a further embodiment of a rotationally asymmetric actuation ring. In the present figure, the actuation ring 85 has an elliptical shape. Again, the actuation ring 85 is coupled to the actuator 40. As the actuator 40 rotates, the actuation ring 85 rotates with it. Before unsealing, the reagent storage containers 1 are positioned towards the longer axis of the ellipse shaped actuation ring 85. As the actuator 40 and, consequently, the actuation ring 85 rotate the centre facing side of the actuator ring 85 starts pushing against the protrusions 55. As a result, the reagent storage containers 1, movable along straight lines through the centre of the actuator 40, moved towards their respective openers 5. The length of the shorter axis of the ellipse shaped actuation ring 85 has been chosen such that the reagent storage containers 1 can be unsealed by their respective openers 5 as the shorter axis nears the reagent storage containers 1 (indicated by the dashed actuation ring 85 and the dashed reagent storage container 1). Once unsealed, reagent can be removed from the reagent storage containers 1, for instance, in the way shown in FIG. 4.

The ellipse shaped actuation ring 85 and the cooperating protrusions 55 have the advantage that the relative position of a reagent storage container 1 and its corresponding opener 5 remain unchanged if the actuator 40 and, consequently, the actuation ring 85 rotate further, after the shorter axis has passed a specific protrusion 55. Once moved towards the centre of the actuator 40, a reagent storage container 1 remains in that position. This has the advantage that the housing 35 and the actuator 40 may be arranged to form a manifold that can couple selectively to one of the reagent storage containers 1. Such a manifold has already been discussed in relation to FIG. 4.

It will be clear to a person skilled in the art that variations on the arrangement shown in the present figure are possible. In the present figure protrusions inside the ellipse shaped actuation ring 85 are moved towards the centre of the ellipse. Alternatively, an ellipse shaped actuation ring may be used to move a reagent storage container or an opener outwards away from the centre of the ellipse. One embodiment of such an arrangement comprises an ellipse shaped actuation ring coupled to an actuator. This embodiment further comprises a reagent storage container positioned near the shorter axis of the ellipse prior to unsealing of the reagent storage container and a corresponding opener facing the sealed portion of the reagent storage container. As the actuator and, consequently, the actuation ring rotate, the reagent storage container moves outwards from the centre of the ellipse as the longer axis of the ellipse nears the reagent storage container. The distance between the reagent storage container and the opener are chosen such that the opener can unsealed the reagent storage container as the longer axis of the ellipse shaped actuation ring nears the position of the reagent storage container.

Figure 6:
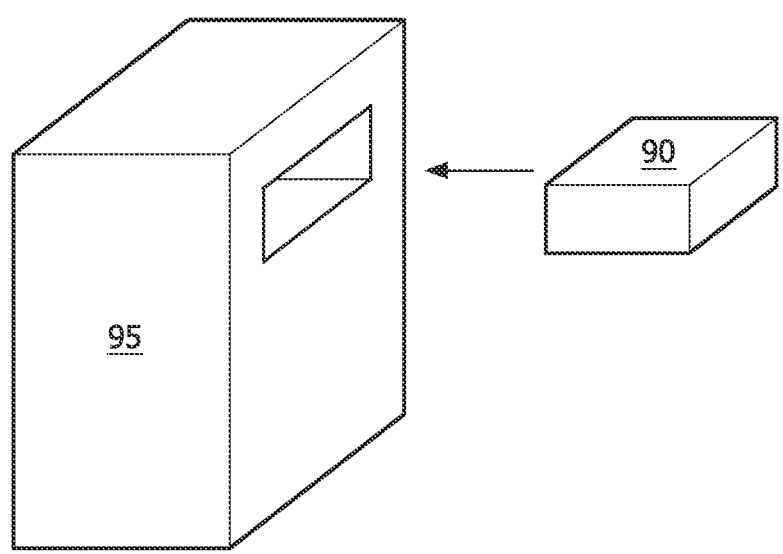
FIG. 6 schematically shows a cartridge according to the invention, the cartridge being insertable into a device for molecular diagnostics testing.

FIG. 6 schematically shows a cartridge according to the invention, the cartridge being insertable into a device for molecular diagnostics testing. The present figure shows a cartridge 90 insertable into a device for molecular diagnostics testing 95. The device for molecular diagnostics testing 95 comprises means for processing the cartridge 90 such as, for instance, heaters and coolers (for instance for use in nucleic acid amplification) and detection means for detecting signals from a sample that is tested. The cartridge 90 comprises a reagent storage container, an opener, and an actuator according to any one of the embodiments of the present invention. Insertion of the cartridge 90 into the device for molecular diagnostics testing 95 is indicated by the arrow.

Figure 7:
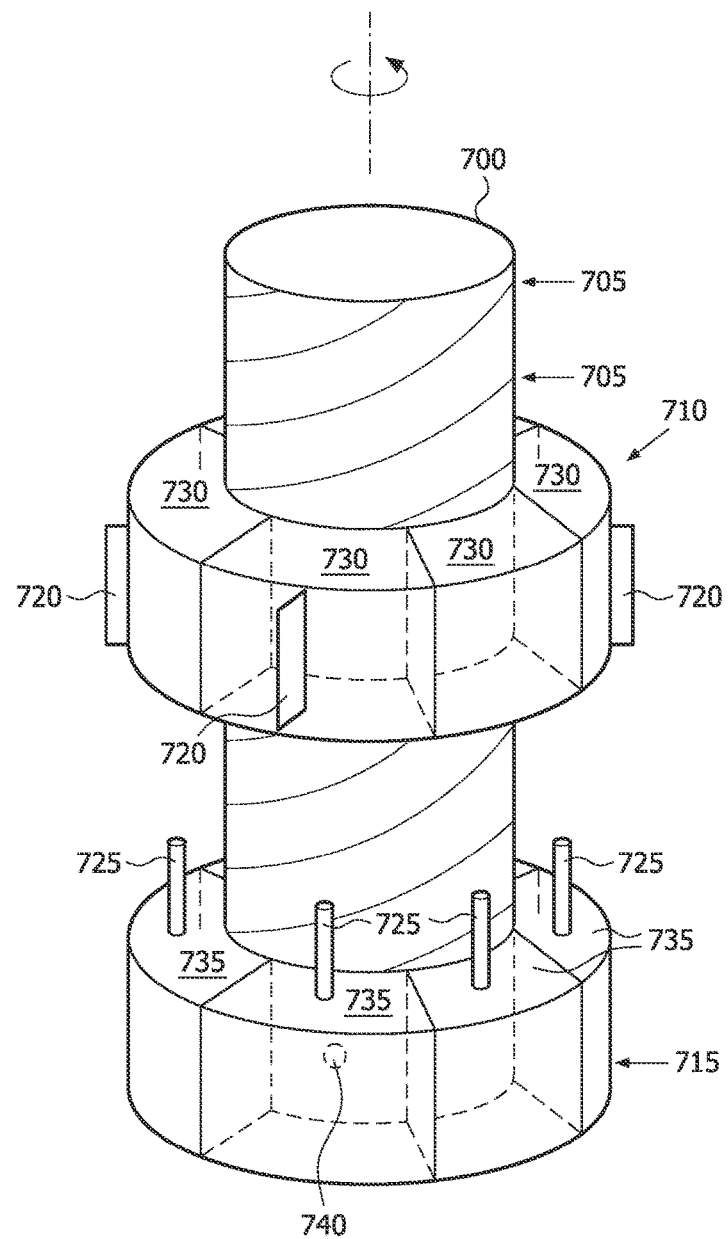
FIG. 7 schematically shows a further device according to the invention wherein the actuator comprises thread for moving a reagent storage container and an opener together.

FIG. 7 schematically shows a further device according to the invention wherein an actuator 700 comprises thread 705 for moving a reagent storage container 710 and an opener 715 together. Turning of the actuator 700, which also functions as a manifold, moves the reagent storage container 710 and the opener 715 towards each other so that the reagent storage container is unsealed by the opener and reagent can be removed from the reagent storage container. The reagent storage container 710 and the opener 715 and move towards each other because at least one of them is connected to a thread cooperating with the thread on the actuator 700. In the present embodiment it is the reagent storage container 710 that is connected to thread that cooperates with the thread of the actuator 700. The reagent storage container 710 is prevented from rotating itself by ribs 720. The ribs 720 are kept in place by cooperating ribs or grooves in the housing in which the device shown in the present figure is placed. The housing is not shown in FIG. 7. It will be clear to a person skilled in the art that numerous other options exist to prevent the reagent storage container 710 (or, alternatively, the opener 715) from rotating. In the present example, the reagent storage container 710 moves towards the opener 715 if the actuator 700 is turned in the proper direction. The opener 715 comprises means 725 for unsealing the reagent storage container 710. The means 725 may comprise, for instance, a pointed tip, a hollow needle, etc. for, for instance, piercing a foil sealing the reagent storage container 710 on the side facing the opener 715. The reagent storage container 710 may comprise one or more storage compartments 730 for storing different reagents. Similarly, the opener 715 may comprise one or more means 725 for unsealing the reagent storage container 710 coupled to opener compartments 735, so that the various storage compartments 730 in the reagent storage container 710 can be unsealed individually. The actuator 700 comprises one or more openings 740 selectively coupling to one or more opener compartments 735. Through such an opening 740 reagent can be removed from a storage compartment 730 comprised in the reagent storage container 710 via the means 725 and an opener compartment 735 for instance by operating a plunger (not shown) inside the actuator 700.

Figure 8:
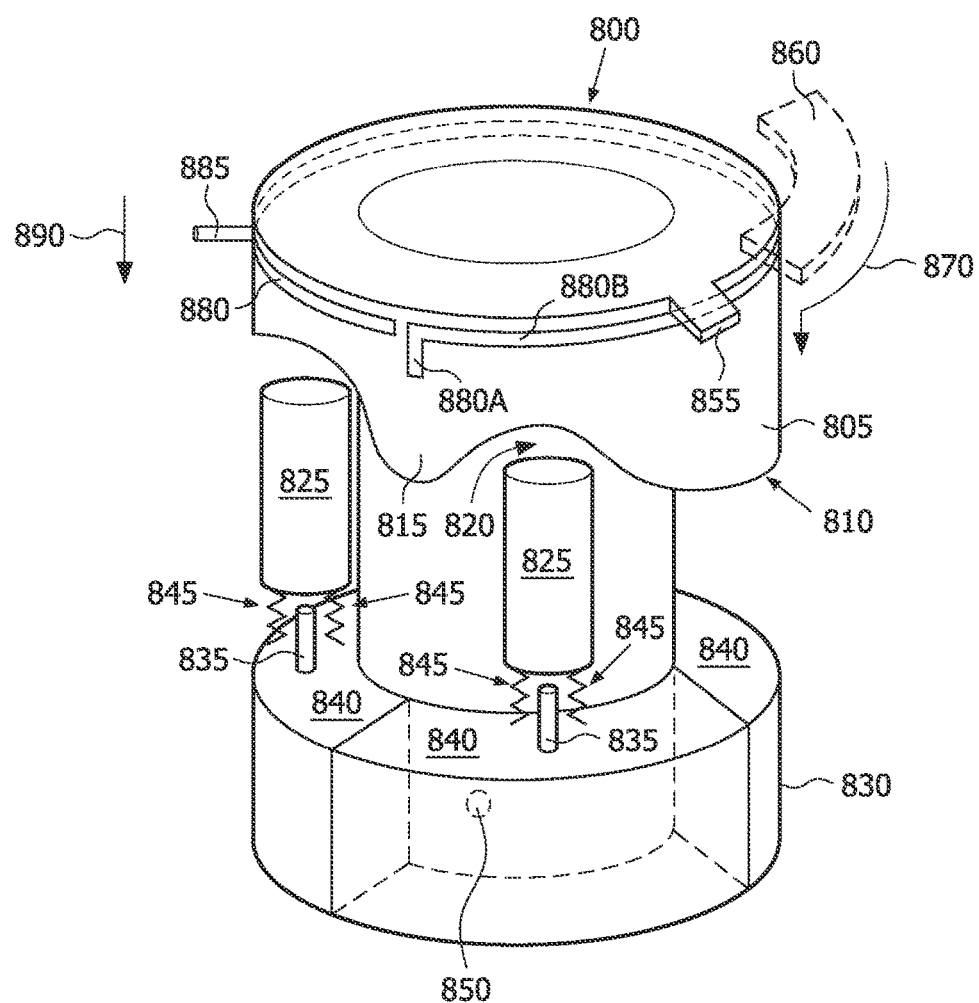
FIG. 8 schematically shows a further device according to the invention wherein the actuator comprises a shaped ring comprising a shaped surface.

FIG. 8 schematically shows a further device according to the invention wherein the actuator 800 comprises a shaped ring 805 comprising a shaped surface 810. The shaped surface 810 comprises one or more 'hills' 815 and 'troughs' 820. The actuator 800 is positioned such that the shaped surface 810 with the hills 815 and troughs 820 faces at least one of a reagent storage container 825 and an opener 830. In the present figure, the shaped 805 ring faces two reagent storage containers 825. Initially, the reagent storage containers 825 are aligned with troughs 820. Turning of the shaped ring 805 then aligns the reagent storage containers 825 with hills 815. As the points of contact between the reagent storage containers 825 and the shaped ring 805 move closer to the crest of a hill 815, the reagent storage containers 825 are pushed towards the opener 830. The reagent storage containers 825 are supported such that they can only move along the line indicated by the arrow 890 (support not shown, but, for instance, a pin/groove support would be suitable). The height of the crest of a hill 815 is such that, at least when the contact point between a reagent storage container 825 and the shaped ring 805 reaches the crest, the reagent storage container 825 is moved over a distance sufficient to have the reagent storage container 825 opened by the opener 830. To this end, the opener 830 comprises one or more means 835 for unsealing one or more reagent storage containers 825. Examples of such means 835 pointed tips, hollow needles, etc. the opener 830 comprises compartments 840 coupled to the means 835. The different compartments 840 may be regarded as separate openers 830. Consequently, separate, mutually disconnected, openers may be used instead of a single opener 830 comprising multiple compartments 840 as shown in the present figure. A reagent storage container 825 may be supported by a support element 845, for instance a resilient element such as a spring, to prevent the reagent storage container 825 from being opened by the opener 830 prior to use of the shaped ring 805 with respect to the reagent storage container 825. As shown in the present figure, the shaped ring 805 may comprise a plurality of hills 815 and troughs 820 to simultaneously support the opening of a plurality of reagent storage containers 825. The amplitudes of the various hills 815 and troughs 820 may be different to allow the sequential opening of different reagent storage containers 825 or to allow more freedom in the positioning of reagent storage containers 825 and their respective means 835 for unsealing (the reagent storage containers 825 and, similarly, their means 835 for unsealing need not lie in a single plane perpendicular to the direction of motion of a reagent storage container 825 and a means 835 for unsealing towards each other. The actuator 800 comprises at least one opening 850 for selectively coupling to a compartment 840 in the opener 830. After unsealing of a reagent storage container 825, reagent may be withdrawn from this reagent storage container 825 via the means 835 and the compartment 840 and the opening 850, for instance, by operating a plunger inside the actuator 800 (plunger not shown).

Clearly, the arrangement of the present figure can also be reversed with the shaped ring 805 moving an opener 830 towards a reagent storage container 825 instead of the other way round as in the present figure. The alternative arrangement simply requires the reagent storage container 825 and the opener a camera 830 to swap places as compared to the arrangement in the present figure.

The present figure also shows a locking means 855 for preventing a reagent storage container 825 from being inadvertently opened by its means 835 for unsealing, for instance during storage of the device. Although it is shown in the present figure, a locking means 855 may be incorporated into any of the embodiments shown in the present application. After all, preventing inadvertent opening would benefit any embodiment. As will be evident to a person skilled in the art, various locking means are possible such as pin and hole/groove arrangements. In the present figure, the means 855 comprise a protrusion that is supported in the housing comprising the actuator 800 over a limited angle of rotation. The housing is only partially shown and the part of the housing supporting the locking means 855 is indicated by the dashed part 860. Once the actuator 800 is rotated over an angle exceeding the angle of rotation over which the protrusion 855 is supported by the housing, the shaped ring 805 is allowed close enough to the reagent storage containers 825 for them to be opened. This latter situation is the situation depicted in FIG. 8. The movement from the locking means 855 from the situation in which it is supported by the dashed part of the housing to the situation in which the locking means 855 are no longer supported is indicated by the arrow 870.

An alternative or additional locking means comprises a groove 880 on the actuator 800 that holds a pin 885 comprised the housing of the actuator 800. Again, these locking means may be combined with any of the previous embodiments of the present invention. For instance during storage of the device shown in FIG. 8, the pin 885 rests in the part of the groove 880 indicated as 880A. With the pin 885 in that position, the actuator 800 is prevented from rotating so that it is unable to move a reagent storage container 825 and its opener 830 towards each other. By moving the actuator 800 slightly in the direction indicated by the arrow 890, the pin 885 is able to enter the part of the grooves 880 indicated as 880B and that extends in the direction of rotation of the actuator 800. Once the pin 885 is in the grooves 880B, the actuator 800 is allowed to rotate so that its shaped surface 805 can interact with a reagent storage container 825 (or an opener 830) to move the reagent storage container 825 and its opener 830 towards each other. Clearly, the position of the grooves 880A and 880B and the pin 885 may be reversed in that the grooves 880A and 880B may be comprised in the housing holding the actuator 800 instead of in the actuator 800 itself and in that the pin 885 may be comprised in the actuator 800. It will also be clear that the grooves 880A and 880B may be repositioned relative to each other such that instead of by moving the actuator 800 in the direction indicated by the arrow 890, the actuator 800 is released by moving the actuator 800 in the opposite direction.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. In the system claims enumerating several means, several of these means can be embodied by one and the same item of computer readable software or hardware. The mere fact that certain measures are recited in mutually different dependent claims does not indicate that a combination of these measures cannot be used to advantage.

The invention claimed is:

1. A device for use in molecular diagnostics testing comprising:
   a sealed reagent storage container;
   an opener configured to unseal the sealed reagent storage container;
   a housing; and
   an actuator located in the housing and coupled to at least one of the sealed reagent storage container and the opener, the actuator being configured to move from a locked position to an unlocked position to bring the sealed reagent storage container and the opener together, and the opener being configured to unseal the sealed reagent storage container in response to a movement of the actuator,
   wherein the actuator includes a locking protrusion which is supportable on a part of the housing,
   wherein the locking protrusion is configured to prevent movement of the sealed reagent storage container and the opener towards each other and away from each other in the locked position when the locking protrusion is supported on the part of the housing, and
   wherein the locking protrusion is configured to allow the movement of the sealed reagent storage container and the opener towards each other and away from each other in the unlocked position when the locking protrusion is not supported on the part of the housing.

2. The device as claimed in claim 1, wherein the actuator is rotatable.

3. The device as claimed in claim 1, wherein the actuator includes a rotationally asymmetrical actuation ring having an asymmetric shape, the rotationally asymmetrical actuation ring being configured to be in a first position when the sealed reagent storage container is disengaged from the opener, and the rotationally asymmetrical actuation ring being configured to force at least one of the sealed reagent storage container and the opener towards each other in a second position of the rotationally asymmetrical actuation ring.

4. The device as claimed in claim 3, wherein the rotationally asymmetrical actuation ring comprises a protrusion configured to move at least one of the sealed reagent storage container and the opener towards each other.

5. The device as claimed in claim 2, wherein the actuator comprises a thread configured to move the sealed reagent storage container and the opener towards each other.

6. The device as claimed in claim 2, wherein the actuator comprises a shaped ring, the shaped ring comprising a non-flat shaped surface facing at least one of the sealed reagent storage container and the opener for moving the sealed reagent storage container and the opener towards each other in a direction of the axis of rotation of the actuator.

7. A device for use in molecular diagnostics testing comprising:
   a sealed reagent storage container;
   an opener configured to unseal the sealed reagent storage container;
   a cartridge configured to be insertable into a device for molecular diagnostics testing;
   a housing located in the cartridge; and
   an actuator located in the housing and coupled to at least one of the sealed reagent storage container and the opener, the actuator being configured to bring the sealed reagent storage container and the opener together in an unlocked position, and the opener being configured to unseal the reagent storage container in response to a movement of the actuator,
   wherein the actuator includes a locking protrusion which is configured to rest in a groove of the housing in a locked position to prevent movement of the sealed reagent storage container and the opener towards each other and away from each other in the locked position, and
   wherein the locking protrusion is configured to not rest in the groove of the housing in the unlocked position.

8. A device for use in molecular diagnostics testing comprising:
   a sealed reagent storage container;
   an opener configured to unseal the sealed reagent storage container;
   a housing; and
   an actuator located in the housing and coupled to at least one of the sealed reagent storage container and the opener, the actuator being configured to move from a locked position to an unlocked position to bring the sealed reagent storage container and the opener together, and the opener being configured to unseal the sealed reagent storage container in response to a movement of the actuator,
   wherein the actuator includes a locking protrusion which is supportable on a part of the housing,
   wherein the locking protrusion is configured to prevent movement of the sealed reagent storage container and the opener towards each other and away from each other in the locked position when the locking protrusion is supported on the part of the housing, and
   wherein the locking protrusion is configured to allow the movement of the sealed reagent storage container and the opener towards each other and away from each other in the unlocked position when the locking protrusion is not supported on the part of the housing,
   wherein the actuator has a groove and the housing has a pin, and wherein the pin rests in a first part of the groove of the housing in a locked position, and rests in a second part of the groove of the housing in an unlocked position.

9. A device for use in molecular diagnostics testing comprising:
   a sealed reagent storage container;
   an opener configured to unseal the sealed reagent storage container;
   a cartridge configured to be insertable into a device for molecular diagnostics testing;
   a housing located in the cartridge; and
   an actuator located in the housing and coupled to at least one of the sealed reagent storage container and the opener, the actuator being configured to bring the sealed reagent storage container and the opener together in an unlocked position, and the opener being configured to unseal the reagent storage container in response to a movement of the actuator,
   wherein the actuator includes a locking protrusion which is configured to rest in a groove of the housing in a locked position to prevent movement of the sealed reagent storage container and the opener towards each other and away from each other in the locked position, and
   wherein the locking protrusion is configured to not rest in the groove of the housing in the unlocked position, wherein the actuator has a groove and the housing has a pin, and wherein the pin rests in a first part of the groove of the housing in the locked position, and rests in a second part of the groove of the housing in the unlocked position.

10. The device as claimed in claim 7, wherein the actuator includes a rotationally asymmetrical actuation ring having an asymmetric shape, the rotationally asymmetrical actuation ring being configured to be in a first position when the sealed reagent storage container is disengaged from the opener, and the rotationally asymmetrical actuation ring being configured to force at least one of the sealed reagent storage container and the opener towards each other in a second position of the rotationally asymmetrical actuation ring.

* * * * *